United States Patent [19]
Carlson et al.

[11] Patent Number: 6,140,065
[45] Date of Patent: Oct. 31, 2000

[54] METHODS FOR DIAGNOSING BENIGN PROSTATIC DISEASES AND PROSTATIC ADENOCARCINOMA USING AN ALGORITHM

[75] Inventors: Grant D. Carlson, Orange; Christina Beth Cavallo-Calvanese, Windsor, both of Conn.

[73] Assignee: Dianon Systems, Inc., Stratford, Conn.

[21] Appl. No.: 08/924,667

[22] Filed: Sep. 5, 1997

[51] Int. Cl.[7] ......................... G01N 33/574; G01N 33/48; A61B 5/00
[52] U.S. Cl. ............................ 435/7.23; 436/64; 128/630
[58] Field of Search ..................................... 435/7.1, 7.23; 436/64; 128/630

[56] References Cited

U.S. PATENT DOCUMENTS 5,710,007  1/1998  Luderer et al. ........................... 435/7.1

OTHER PUBLICATIONS

Baldalament et al. "An algorithm for predicting nonorgan confined prostate cancer using the results obtained from sextant core biopsies with prostate specificd antigen level" The Journal of Urology. vol. 156. pp. 1375–1380, Oct. 1996.

*Primary Examiner*—Yvonne Eyler
*Attorney, Agent, or Firm*—Brian D. Voyce

[57] ABSTRACT

The present invention relates to novel reflex methods for identifying a male human patient as suitable for diagnosis either benign prostatic diseases (BPD), (such as benign prostatic hyperplasia, prostatitis, or glandular atrophy), or prostatic adenocarcinoma (CAP) without requiring a biopsy. The method requires measuring two biochemical markers and knowing the patient age. The total prostate specific antigen (PSA) level in the blood or serum of the patient is measured. If the patient has a total PSA level of between 4.0 ng/mL and 20.0 ng/mL, then the free PSA level in the blood or serum of the patient is measured. The proportion of free PSA to total PSA is calculated. The patient's age is noted, rounding down to an integral numbers of years. The two measured values and the age are entered into a particular identifying algorithm which is derived from a logistic regression model. If a value of greater than about 0.18 is generated from entering these values into the algorithm, then the patient is diagnosed as having CAP. If value of less than or equal to about 0.18 is generated from entering these values into the algorithm, then the patient is diagnosed as having BPD.

2 Claims, 6 Drawing Sheets

METHODS FOR DIAGNOSING BENIGN PROSTATIC DISEASES AND PROSTATIC ADENOCARCINOMA USING AN ALGORITHM

TECHNICAL FIELD

The present invention relates to novel reflex methods for identifying a male human patient as suitable for diagnosis either benign prostatic diseases (BPD), (such as benign prostatic hyperplasia, prostatitis, or glandular atrophy), or prostatic adenocarcinoma (CAP) without requiring a biopsy. The method requires measuring two biochemical markers and knowing the patient age. The total prostate specific antigen (PSA) level in the blood or serum of the patient is measured. If the patient has a total PSA level of between 4.0 ng/mL and 20.0 ng/mL, then the free PSA level in the blood or serum of the patient is measured. The proportion of free PSA to total PSA is calculated. The patient's age is noted, rounding down to an integral numbers of years. The two measured values and the age are entered into a particular identifying algorithm which is derived from a logistic regression model. If a value of greater than about 0.18 is generated from entering these values into the algorithm, then the patient is diagnosed as having CAP. If value of less than or equal to about 0.18 is generated from entering these values into the algorithm, then the patient is diagnosed as having BPD.

BACKGROUND ART

Prostate specific antigen (PSA) is recognized as a molecular marker for CAP. Blood or serum based immunoassays measuring the total PSA level have been commercially available for a number of years. However, the detection of total PSA does not necessarily mean that a patient has CAP. In order to distinguish CAP, a total PSA test has to satisfy two elements: a high sensitivity—the ability to detect disease when present, and a high specificity—the ability to detect true negatives and avoid false positives. From clinical experience, total PSA tests have become generally accepted as being predictive of CAP if the total PSA level is greater than 10.0 ng/mL. Total PSA values between 0.0 ng/mL and about 4.0 ng/mL have been considered generally predictive of no disease being present, with a reference value of about 3.5 ng/mL being used for men under 60 years old and about 2.5 ng/mL being used for men under 50 years old. (See Oesterling, J. E., Cooner, W. H., Jacobsen, S. J., Guess H. A., and Lieber, M. M.: *"Influence of Patient Age on the Serum PSA Concentration and Important Clinical Observations"*: Urol. Clin. North Am.; Vol. 20: 671–680, 1993.)

PSA is primarily organ-specific, not cancer specific. Thus, PSA in blood or serum can result not only from CAP, but also from normal or hyperplastic prostate tissues. Historically, a total PSA test cannot reliably distinguish BPD from CAP at less than 10.0 ng/mL. Studies have found that 43% (136/319) of patients with organ-confined CAP have a total PSA value within the normal range of less than 4.0 ng/mL. Moreover, about 25% (148/597) of men with BPD have a total PSA value above 4.0 ng/mL. (See Oesterling, J. E.: *"Prostate Specific Antigen: A Critical Assessment of the Most Useful Tumor Marker for Adenocarcinoma of the Prostate"*, J. Urol., Vol:145:907–923, 1991.) Standard medical practice is to biopsy men over 60 years of age having total PSA levels of between 4.0 ng/mL and 10.0 ng/mL because about 30% of those patients have CAP. Likewise, age specific reference ranges have been used for patients between 50 years and 60 years old whose total PSA falls between 3.5 ng/mL and 10.0 ng/mL and patients under 50 years old whose total PSA falls between 2.5 ng/mL and 10.0 ng/mL. These men are often biopsied under current medical practice.

One proposed method for detecting CAP is disclosed in U.S. Pat. No. 5,501,983 to Hans Lilja et alia. In general, the Lilja patent discloses using immunoassays to measure free PSA and a complexed form of PSA. Free PSA is a 33 kDa single chain glycoenzyme that is produced by the epithelial cells lining the acini and prostatic ducts of the prostate gland. Complexed PSA refers primarily to a 90kDa complex of PSA bound to alpha 1-antichymotrypsin (ACT) protein, an endogenous protease inhibitor. Free PSA and complexed PSA, and their proportions are applied in the diagnosis of patients with CAP. Throughout, the specification discloses using a combination of a free PSA to total PSA (F/T) proportion and a complexed PSA to total PSA (C/T) proportion for use in diagnosing CAP. No prostate needle biopsy were performed on the patients, and the patients covered a full range of total PSA values. The text provides no guidance as to specifically how one uses these proportions. It should be noted that the initial discovery of the protein designated as free PSA was reported by George Sensabaugh et alia in an article entitled *"Isolation and Characterization of a Semen-Specific Protein from Human Seminal Plasma: A Potential New Marker for Semen Identification"*, J. Forensic Sci., 1978; 23:106–118. Therein, Sensabaugh disclosed the free PSA protein as the prostate protein "p30", having a molecular weight of about 30,000 daltons. This find was confirmed in U.S. Pat. No. 4,446,122 to Tsann M. Chu and Lawrence Papsidero, but here the protein was designated as "PA".

A significant advance in diagnosing BPD in a male human patient without requiring a biopsy is disclosed by Luderer, A. A., et alia in *"Measurement of the Proportion of Free to Total Prostate-Specific Antigen Improves Diagnostic Performance of Prostate-Specific Antigen in The Diagnostic Gray Zone of Total Prostate-Specific Antigen"*, Urol., Vol. 46: 187–194, 1995. This reflex method eliminates the need for about one-third of those patients with benign disease to undergo such a biopsy. For those patients in the gray diagnostic zone, the method comprises four steps. First, one measures the total PSA level in the blood or serum of the patient. Second, one measures the free PSA level in the blood or serum of a patient, but only if he has a total PSA level of between about 2.5 ng/mL and about 10.0 ng/mL. If the patient has a total PSA level below 2.5 ng/mL, then he is diagnosed to have BPD. If the patient has a total PSA level above 10.0 ng/mL, then he is presumed to have CAP and must be biopsied. Third, one calculates the proportion of free PSA to total PSA. Fourth and finally, one diagnoses the patient as having BPD if the calculated proportion of free PSA to total PSA is greater than about 25%.

Another recent significant advance in diagnosing CAP in a male human patient is disclosed by Chen et alia in *"Using Proportions of Free to Total Prostate-Specific Antigen, Age, and Total Prostate-specific Antigen to Predict the Probability of Prostate Cancer"*, Urol., Vol. 47(4): 518–524, 1996. The Chen reflex method comprises four steps. The total prostate specific antigen (PSA) level in the blood or serum of the patient is measured. If the patient has a total PSA level of between 2.5 ng/mL and 20.0 ng/mL, then the free PSA level in the blood or serum of the patient is measured. The proportion of free PSA to total PSA is calculated. If this proportion is less than about 7%, then the patient is diagnosed as having CAP.

DISCLOSURE OF THE INVENTION

The present invention relates to a reflex method for diagnosing BPD in a male human patient without requiring a biopsy. The present method is unexpectedly better than the Luderer method while maintaining the performance of the Chen method. The need for about 35% of the patients with BPD in the gray diagnostic zone of 4.0 ng/mL to 10.0 ng/mL total PSA to undergo such a biopsy is eliminated, and the need for about 29% of the patients with BPD having a total PSA of between 10.1 ng/mL and 20.0 ng/mL to undergo such a biopsy is also eliminated. This is opposed to about 16% of the patients with BPD in the gray diagnostic zone of 4.0 ng/mL to 10.0 ng/mL total PSA having to undergo such a biopsy and about 14% of the patients with BPD having a total PSA of between 10.1 ng/mL and 20.0 ng/mL having to undergo such a biopsy with the Luderer and Chen methods.

As a reflex method, five steps are involved in the present invention. First, one measures the total PSA level in the blood or serum of the patient. Second, one measures the free PSA level in the blood or serum of a patient, but only if he has a total PSA level of between about 4.0 ng/mL and about 20.0 ng/mL. If the patient has a total PSA level below 4.0 ng/mL, then he is diagnosed to have BPD. If the patient has a total PSA level above 20.0 ng/mL, then he is presumed to have CAP and must be biopsied. Third, one determines an age factor by rounding down the age of the patient to the nearest integral number. (For example, a patient who is 65 years and 7 months old is given an age factor of 65 years, not 66 years). Fourth, one enters the total PSA value, the free PSA to total PSA proportion value, and the age factor into an identifying algorithm. The identifying algorithm is as follows:

$$PV = P_1/(1+P_1),$$

in which $P_1 = e^x$,
where $x = [(-1.8075) + (-0.3297 * A_1 P_1) + (-0.3592 * A_2 P) + (-0.1242 * A_3 P_3) + (0.0591 * AGE) + (0.1509 * \ln(PSA_T)) + (-1.1915 * \ln(F:T))]$, and in which F:T = the proportion of the free PSA value to total PSA value $A_1 P_1 = 1$ if AGE=61 to 67 and F:T=16 to 20, otherwise $A_1 P_1 = 0$;

$A_2 P = 1$ if AGE=68 to 72 and $PSA_T$ is greater than 10, otherwise $A_2 P = 0$; and $A_3 P_3 = 1$ if AGE is equal to or greater than 73 and F:T is equal to or less than 10, otherwise $A_3 P_3 = 0$.

One can either enter a precalculated free PSA to total PSA proportion (F:T) into the algorithm or one can enter a separate free PSA value (F) and total PSA value (T) and divide the former by the latter as part of the solution of the algorithm. Fifth, and finally, one identifies the patient either as having BPD if the probability value (PV) generated by the algorithm is less than or equal to about 0.18 or less or as having CAP if the probability value is greater than about 0.18.

The present invention also comprises an electronic device that contains the algorithm in an executable form for calculating a probability value when supplied with data input of the requisite variables. A memory storage device has the identifying algorithm stored thereon in a readable format and an input means for entering and storing the age variable, the free PSA variable, and the total PSA variable. Such information can be executable for query and report compilation by a relational database management system run on a computer. The medium storage device can comprise either a magnetic storage element, an optical storage element, or a programmable chip such as an EPROM device. A preferred device would incorporate an electronic microprocessor that can calculate a probability value from the stored identifying algorithm and the entered results of an analysis of a biological sample from at least one patient in which total PSA and free PSA are measured and the patient age is known. In addition, the device can have an output means for transmitting the calculated probability value to a relational database program for storage, to a printer, or to a monitor. As an alternative to transmitting the actual calculated probability value, the output means can communicate either a "yes"/ "no" or a "cancer" or "benign" result based on the calculated probability value being compared to a predetermined cutoff level of 0.18 for that probability value. "Yes" or "Cancer" would be for identifying a patient as suitable for a diagnosis of CAP if the probability value is greater than about 0.18, otherwise the result would be "No" or "Benign", meaning identifying the patient as suitable for a diagnosis of BPD.

BEST MODES FOR CARRYING OUT THE INVENTION

Identifying Algorithm

Figure 1:
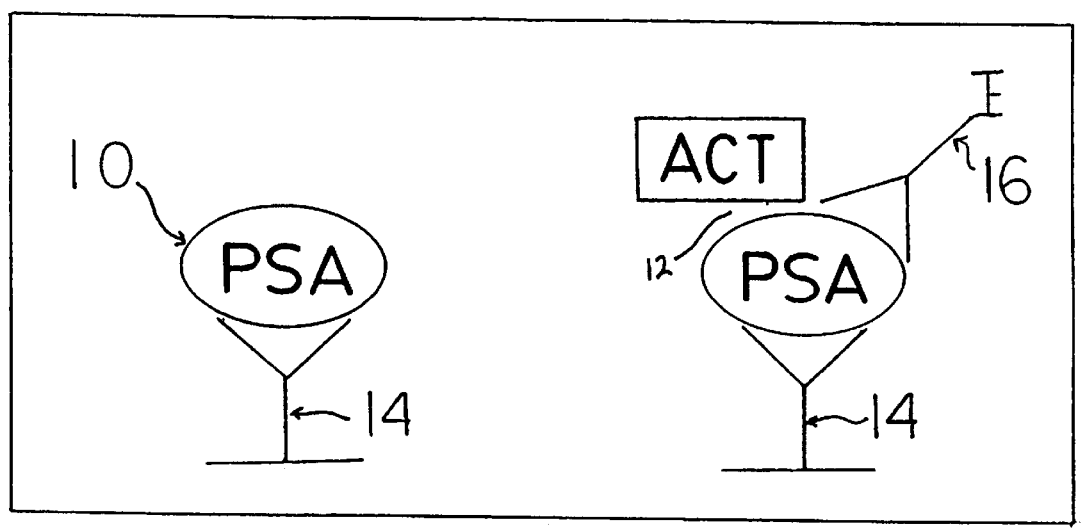
FIG. 1 is a diagrammatic view of the total PSA assay used in the present invention.

The algorithm is a logisitic regression model with the variables of age, the natural log transform of total PSA, the natural log transform of percent free PSA, and design variables for a first interaction between patient age and total PSA and a second interaction between patient age and percent free PSA.

Malignancy rates increased linearly with age, the natural log transform of total PSA, and the natural log of percent free PSA. Therefore, patient age, the natural log transform of total PSA and the natural log transform of percent free PSA were all included in the identifying algorithm as continuous variables. Table 1 illustrates the interaction between total PSA and patient age. Men between 45 years and 55 years old showed a 5 percentage point increase in malignancy rates if they had a total PSA value between 10.1 ng/mL and 20.0 ng/mL, as opposed to a value between 4.0 ng/mL and 10.0 ng/mL. For men greater than 75 years old, the percentage point increase was 17. An interaction exists between age and total PSA because cancer rates based on total PSA increased faster in older men than in younger men by 12 percentage points. Thus, as patient age increases, more emphasis should be placed on total PSA if one is calculating a patient's risk for CAP.

TABLE 1

Observed Malignancy Rates by Age and Total PSA
Total PSA range (ng/mL)

| Age (Integer Years) | 4.0 to 10.0 | 10.1 to 20.0 | Total |
| --- | --- | --- | --- |
| 45–55 | 22% (349) | 27% (68) | 22% (417) |
| 56–65 | 29% (1211) | 35% (246) | 30% (1457) |

TABLE 1-continued

Observed Malignancy Rates by Age and Total PSA
Total PSA range (ng/mL)

| Age (Integer Years) | 4.0 to 10.0 | 10.1 to 20.0 | Total |
|---|---|---|---|
| 66–75 | 34% (1479) | 40% (460) | 35% (1939) |
| >75 | 45% (346) | 62% (139) | 50% (485) |
| Total | 32% (3385) | 41% (913) | 34% (4298) |

Table 2 illustrates the interaction between free PSA to total PSA proportion and patient age. Men between 45 years and 55 years old showed a 31 percentage point increase in malignancy rates if they had a free PSA to total PSA proportion of less than 7% as compared to those having a free PSA to total PSA proportion of at least 25%. For men greater than 75 years old, the percentage point increase was 48. An interaction exists between age and free PSA to total PSA proportion because malignancy rates based on F:T PSA increased faster in older men than in younger men by 17 percentage points. Thus, as patient age increases, free PSA to total PSA plays a more significant role when determining a patient's risk for CAP.

TABLE 2

Observed Malignancy Rates by Age and Free to Total PSA Proportion

| Age* | <7% | 7%–15% | 15% to 25% | >25% | Total |
|---|---|---|---|---|---|
| 45–55 | 38% (50) | 26% (248) | 9% (104) | 7% (15) | 22% (417) |
| 56–65 | 56% (91) | 37% (716) | 20% (526) | 13% (124) | 30% (1457) |
| 66–75 | 61% (91) | 45% (813) | 27% (762) | 16% (251) | 35% (1939) |
| >75 | 68% (31) | 64% (212) | 43% (168) | 20% (74) | 50% (485) |
| Total | 56% (285) | 42% (1989) | 25% (1560) | 16% (464) | 34% (4298) |

*(Integer Years)

Table 3 illustrates the lack of significant interaction between free PSA to total PSA proportion and total PSA. The risk of CAP for a patient with a total PSA value between 4.0 ng/mL and 10.0 ng/mL showed a 38 percentage point increase in malignancy rates while those between 10.1 ng/mL and 20.0 ng/mL showed a 40 percentage point increase. Thus, there does not appear to be a significant interaction between free PSA and total PSA.

TABLE 3

Observed Malignancy Rates by Age and Free PSA to Total
PSA Proportion

| Total PSA * | <7% | 7%–15% | 15% to 25% | >25% | Total |
|---|---|---|---|---|---|
| 4.0 to 10.0 | 53% (186) | 40% (1528) | 24% (1291) | 15% (380) | 32% (3385) |
| 10.1 to 20.0 | 61% (99) | 48% (461) | 29% (269) | 21% (84) | 41% (913) |
| Total | 56% (285) | 42% (1989) | 25% (1560) | 16% (464) | 34% (4298) |

* (Range in ng/mL)

Adjustments have been made to the probabilities for the interactions between age and percent free PSA with design variables. These variables take effect when a patient's age is either between 61 and 67 years old and the patient's free PSA to total PSA proportion is between 16% and 20%, and also when a patient's age is greater than 73 years and their free PSA to total PSA proporiton is less than or equal to 10%. An adjustment has also been made to the probability with a design variable when the patient's age is between 68 and 72 years of age and their total PSA value is greater than 10 ng/mL.

Assays

In preferred embodiments described below, the present method uses two immunoassays, however any specific binding assay that measures either free PSA or total PSA is suitable for the present methods. The first assay is a total PSA sandwich immunoassay manufactured by Tosoh Medics, Inc. (Tosoh) of Foster City, Calif., and performed on the Tosoh AIA-1200 automated immunoassay device. The assay is an immunoenzymetric assay using dual murine monoclonal antibodies. FIG. 1 shows diagrammatically how, in the final sandwich configurations, this first assay captures both free PSA (10) and complexed PSA/ACT (12) using a capture antibody (14) and an enzyme labeled antibody (16).

Figure 2:
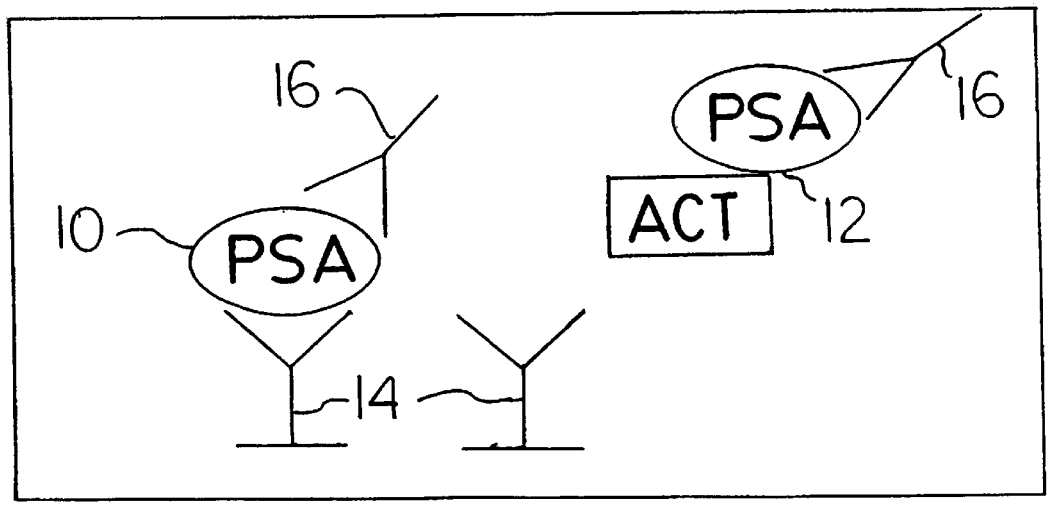
FIG. 2 is a diagrammatic view of the free PSA assay used in the present invention.

The second assay is a free PSA immunoassay manufactured developed by Immuno Corp. for Dianon Systems, Inc. (Dianon) of Stratford, Conn. This free PSA test is designed to detect free PSA in serum using an IRMA coated tube format. Free PSA binds to a tube coated by a monoclonal antibody which selectively binds free PSA but not complexed PSA. After washing, an $I^{125}$ labeled polyclonal antibody against free PSA is reacted with the bound free PSA. The physician is given a result that expresses a proportion of free PSA to total PSA. FIG. 2 shows diagrammatically how in the final sandwich configuration, this second assay captures free PSA (10), but the capture antibody (14) does not specifically bind to the complex of the PSA/ACT complex (12) and radiolabelled antibody (16).

EXAMPLE 1

Patients

In a clinical study used to construct the algorithm used in the present invention, 3773 urologically referred patients were tested. Classified as "BPD", 2539 males were identified as being between 45 years old and 92 years old, having BPD histologically confirmed by sextant needle prostate biopsy, and no history of cancer. The age mean was 65.6 years. Classified as "CAP", 1234 males were identified as being between 45 years old and 92 years old and having primary CAP histologically confirmed by needle prostate biopsy. The age mean was 68.2 years. For the CAP patients, Gleason scores were distributed as follows: 4 had a Gleason score of 4; 864 had a Gleason score of 5 or 6; 332 had a Gleason score of 7; and 33 had a Gleason score of 8 or 9. Biopsies were performed within 60 days of serum specimen collection. Total PSA was measured using the Tosoh assay described above, in accordance with the manufacturer's instructions. Free PSA was measured using the Dianon assay described above, in accordance with the manufacturer's instructions.

Figure 3:
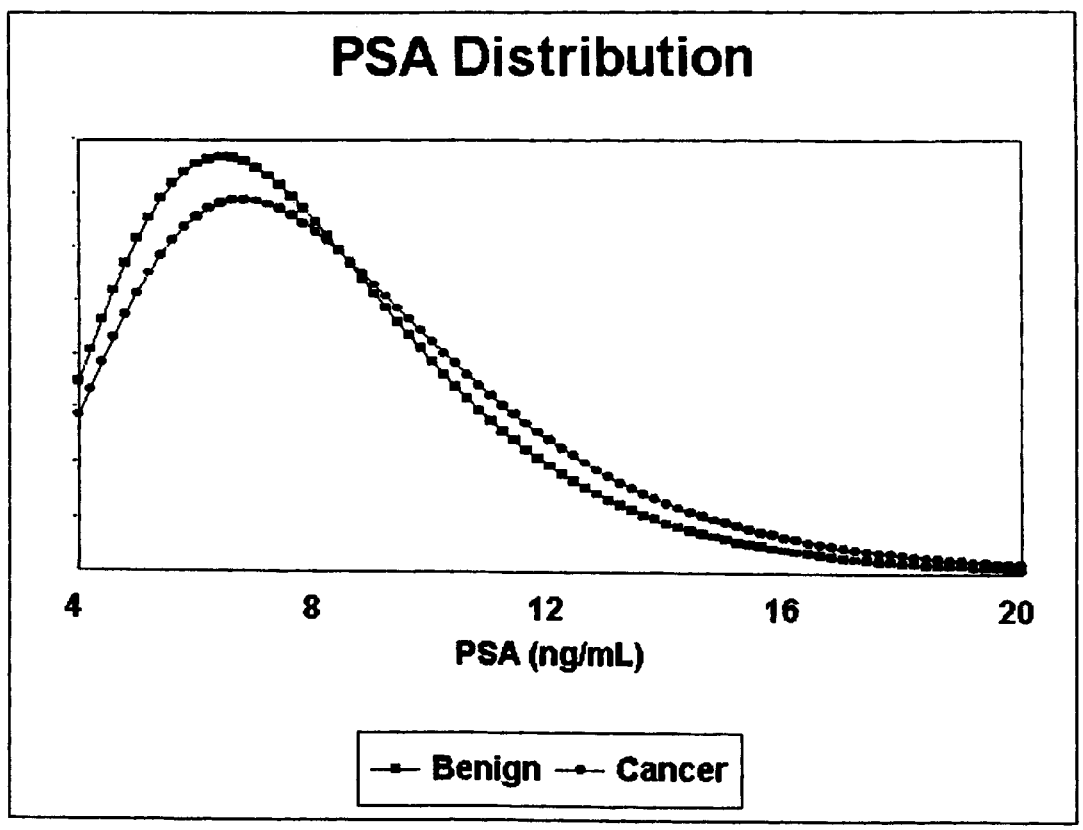
FIG. 3 is a graph showing the distribution of total PSA levels for BPD patients and CAP patients in Example 1.
Figure 4:
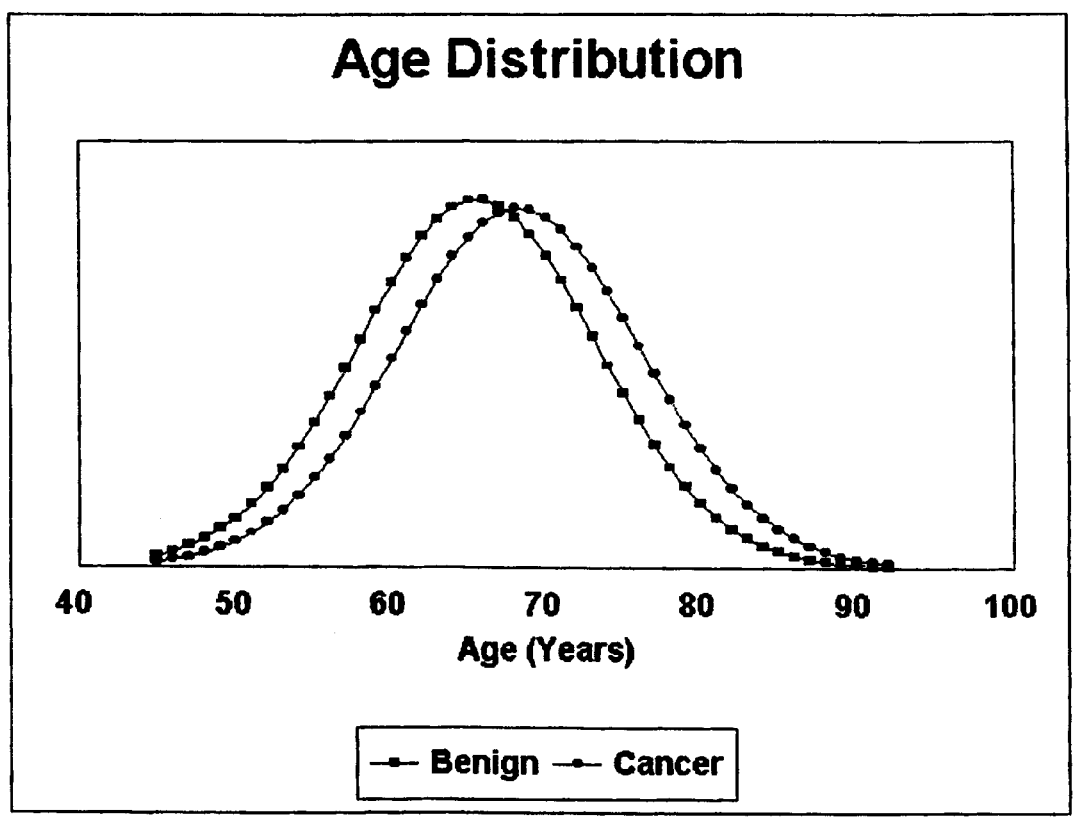
FIG. 4 is a graph showing the distribution of age for BPD patients and CAP patients in Example 1.

FIGS. 3 and 4 illustrate the extent to which the respective variables of age and total PSA distribution do not distinguish well between CAP and BPD populations.

Figure 5:
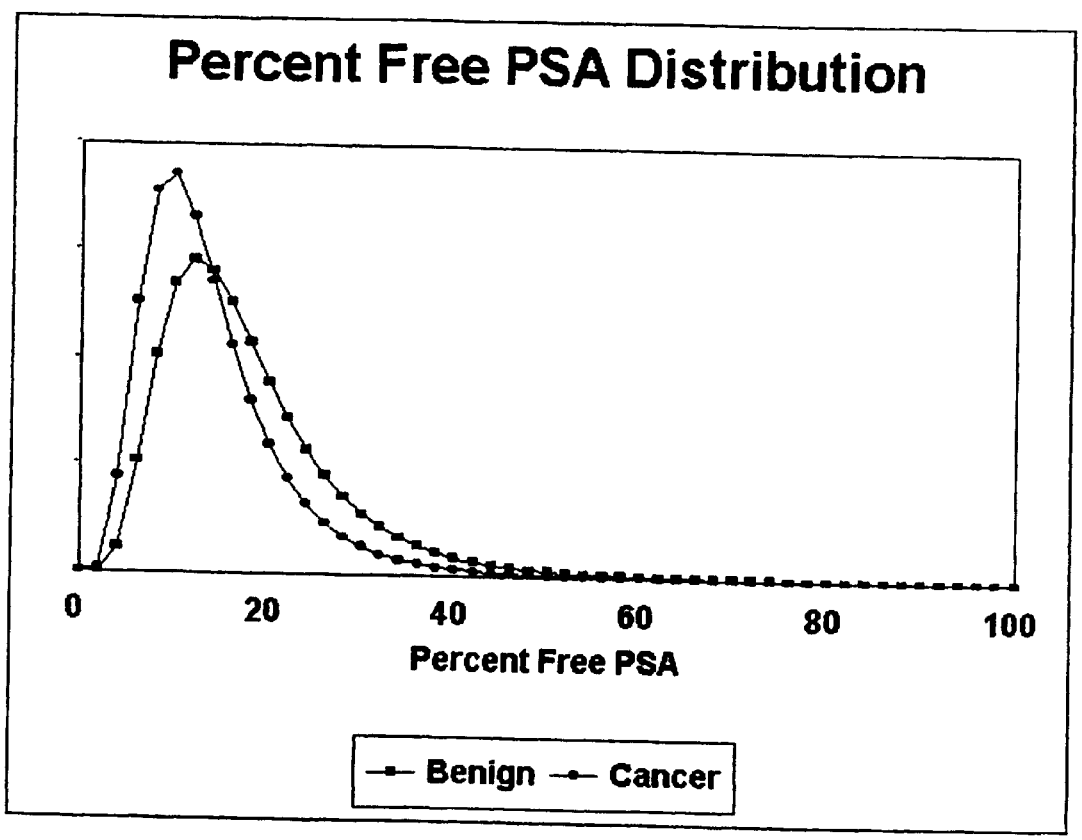
FIG. 5 is a graph showing the distribution of F/T proportions for BPD patients and CAP patients in Example 1.

If the patients are restricted to those having a total PSA of from about 4.0 ng/mL to about 20.0 ng/mL, and the Luderer reflex method is applied, the following results are obtained, as shown in Table 4 and FIG. 5.

TABLE 4

| F/T PSA Proportion | Sensitivity | Specificity |
|---|---|---|
| ≦25% | 94% | 15% |

Sensitivity is reported with respect to CAP, thus at an F/T proportion of ≧25%, the 94% figure means that essentially most CAP patients are present. Conversely, at an F/T proportion of >25% essentially few CAP patients, only BPD patients are present. While these results are better than using total PSA alone, they are not as effective in discriminating between malignant diseases and benign diseases as the present method.

EXAMPLE 2

Validation of the Use of the Identifying Algorithm

In a clinical study to validate the present invention for patients traditionally diagnosed as having CAP, the identifying algorithm was applied to results from testing of 525 additional cases. Classified as "BPD", 398 males were identified as being between 47 years old and 86 years old, having benign prostate disease histologically confirmed by sextant needle prostate biopsy, and no history of cancer, even though they each had a total PSA blood level of between 4.0 ng/mL and 20.0 ng/mL. The age mean was 64.8 years. Classified as "CAP", 266 males were identified as being between 45 years old and 85 years old, having a total PSA level of between 4.0 ng/mL and 20.0 ng/mL, and having primary CAP histologically confirmed by needle prostate biopsy. The age mean was 66.4 years.

Figure 6:
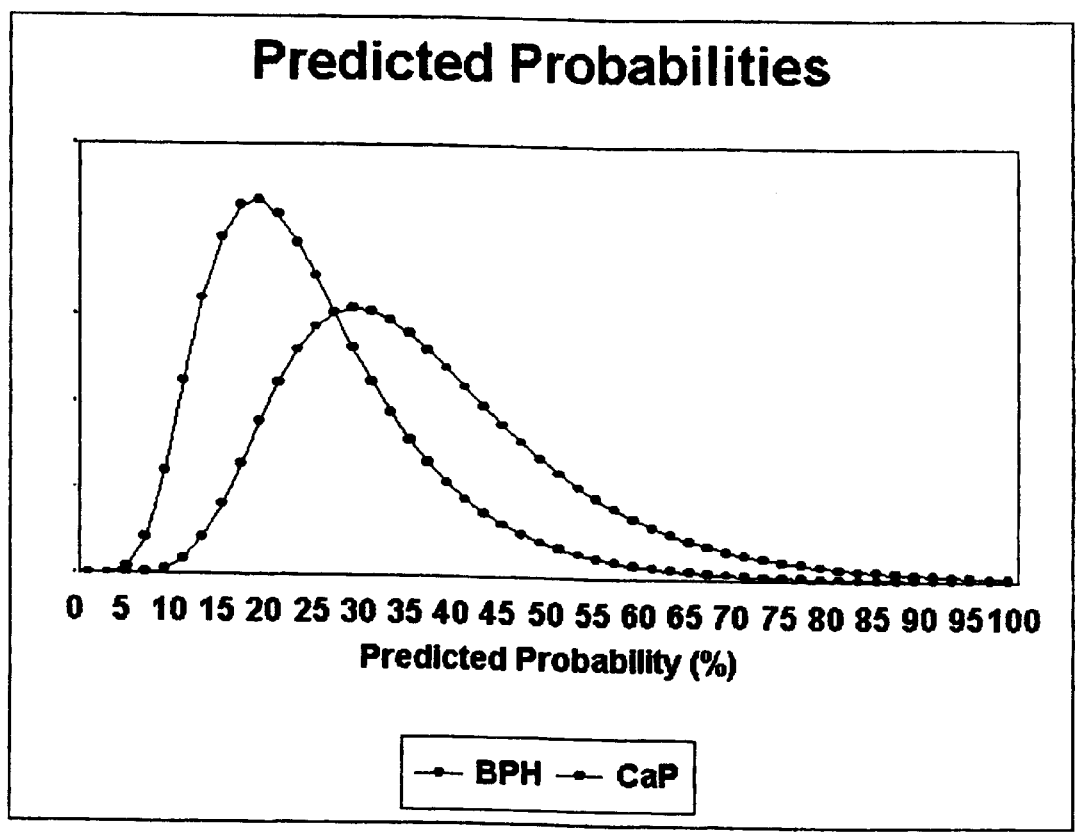
FIG. 6 is a graph showing lognormal distributions of probabilities for BPD patients and CAP patients in Example 1.

Using the identifying algorithm, input from the three variables, and a probability value of greater than 0.18 to be at risk of having CAP, a sensitivity of 95% and a specificity of 34% was achieved. (See FIG. 6). The number of BPD cases correctly identified using the 0.18 probability value cutoff was 48% greater than the number identified using the 25% free PSA to total PSA cutoff value alone, as in the Luderer method. By using a probability value of 0.20, the sensitivity dropped to 90% while the specificity increased to 42% of patients with BPD.

The probability values calculated by the identifying algorithm can also be expressed in the form of a percentage. In other words, 0.18 equals 18%. Such usage is merely for convenience if a physician is used to seeing percentage values, and does not affect the predictive abilities of the present invention. However, one should not confuse a proportion of two laboratory results, such as free PSA (ngmL) to total PSA (ng/mL) with a probability risk of prostate cancer that predicts the proportion of men with prostate cancer to the total number of men with the same variable results.

All publications or unpublished patent applications mentioned herein are hereby incorporated by reference thereto.

Other embodiments of the present invention are not presented here which are obvious to those of skill in the art, now or during the term of any patent issuing herefrom, and thus, are within the spirit and scope of the present invention.

We claim:

1. A method for differentiating a male human patient with either benign prostatic diseases (BPD) or prostatic adenocarcinoma (CAP) comprising:

a) measuring the total prostate specific antigen (PSA) level in the blood or serum of the patient;

b) measuring the free PSA level in the blood or serum of a patient only if the patient has a total PSA level of between about 4.0 ng/mL and about 20.0 ng/mL;

c) calculating an age factor for the patient wherein said age factor is the actual age rounded to the nearest whole integer;

d) calculating a probability value (PV) by entering as variables the total PSA level ($PSA_T$), the free PSA to total PSA proportion level (F:T), and the age factor (AGE) into a diagnostic algorithm wherein $PV=P_1/(1+P_1)$, in which $P_1=e^x$, where $x=[(-1.8075)+(-0.3297*A_1P_1)+(-0.3592*A_2P)+(-0.1242*A_3P_3)+(0.0591*AGE)+(0.1509*\ln(PSA_T))+(-1.1915*\ln(F:T))]$, and in which F:T=the free PSA to total PSA proportion; $A_1P_1=1$ if AGE=61 to 67 and F:T=16 to 20, otherwise $A_1P_1=0$; $A_2P=1$ if AGE=68 to 72 and $PSA_T$ is greater than 10, otherwise $A_2P=0$; and $A_3P_3=1$ if AGE is equal to or greater than 73 and F:T is equal to or less than 10, otherwise $A_3P_3=0$; and wherein * indicates multiplication, and;

e) identifying the patient either as having CAP if the calculated probability value is greater than about 0.18 or as having BPD if the calculated probability value is less than or equal to about 0.18.

2. The method of claim 1 wherein the patient also has a negative prostate biopsy.

* * * * *